(12) United States Patent
Okawa et al.

(10) Patent No.: US 7,314,580 B2
(45) Date of Patent: Jan. 1, 2008

(54) COMPOUND, LIQUID-CRYSTAL COMPOSITION AND OPTICAL MATERIAL

(75) Inventors: Atsuhiro Okawa, Minami-ashigara (JP); Masaki Noro, Minami-ashigara (JP)

(73) Assignee: Fujifilm Corporation, Minato-Ku, Tokyo (JP)

( * ) Notice: Subject to any disclaimer, the term of this patent is extended or adjusted under 35 U.S.C. 154(b) by 130 days.

(21) Appl. No.: 11/075,913

(22) Filed: Mar. 10, 2005

(65) Prior Publication Data

US 2005/0199856 A1 Sep. 15, 2005

(30) Foreign Application Priority Data

Mar. 10, 2004 (JP) ............................. 2004-067079

(51) Int. Cl.
- *C09K 19/34* (2006.01)
- *C09K 19/20* (2006.01)
- *C07D 239/06* (2006.01)
- *C07D 213/30* (2006.01)
- *C07D 213/61* (2006.01)
- *C07C 25/24* (2006.01)

(52) U.S. Cl. ......................... 252/299.61; 252/299.67; 544/335; 546/302; 570/128

(58) Field of Classification Search ................. 428/1.1; 252/299.61, 299.67; 544/335; 546/302; 570/128

See application file for complete search history.

(56) References Cited

U.S. PATENT DOCUMENTS 7,128,953 B2 * 10/2006 Ohkawa et al. ............ 428/1.31

FOREIGN PATENT DOCUMENTS

JP 2003-131035 * 5/2003

* cited by examiner

*Primary Examiner*—Shean C Wu
(74) *Attorney, Agent, or Firm*—Buchanan Ingersoll & Rooney PC

(57) ABSTRACT

Disclosed is a liquid-crystal composition capable of providing a functional film that exhibits useful optical properties. The composition comprises a compound of the following formula (1) that exhibits a smectic liquid-crystal phase.

$$R^1-(Ar^1)_p-C\equiv C-(Ar^2)_m-C\equiv C-(Ar^3)_n-R^2 \qquad (1)$$

wherein $R^1$ and $R^2$ represent alkyl; $R^3$, $R^4$, $R^5$ and $R^6$ represent hydrogen or alkyl; $Ar^1$, $Ar^2$ and $Ar^3$ represent divalent aromatic hydrocarbon or aromatic heterocyclic group; and p, m and n are 1 or 2.

20 Claims, No Drawings

COMPOUND, LIQUID-CRYSTAL COMPOSITION AND OPTICAL MATERIAL

BACKGROUND OF THE INVENTION

1. Field of the Invention

The present invention relates to a novel compound that exhibits a liquid-crystal phase (hereinafter this may be referred to as "liquid-crystal compound"), and to a liquid-crystal composition and an optical material containing the compound. In particular, the invention relates to the liquid-crystal compound of such that its birefringence is large, the angle between the helical axis direction of the helical structure of the liquid-crystal phase of the compound and the major axis direction of the liquid-crystal molecule is large and the temperature range in which the compound exhibits a smectic phase is broad, and also relates to a liquid-crystal composition containing the compound.

2. Description of the Related Art

A liquid-crystal compound is roughly grouped into nematic, smectic and discotic liquid crystals from the molecular morphology and the molecular arrangement thereof. Of those, the smectic liquid crystal has a layered structure and is characterized in that it has a high-order structure. It is known that the smectic liquid crystal which exhibits a helical structure has useful optical properties of birefringence, optical rotation, polarization separation, diffraction, selective reflection, etc.

An optical film that expresses anisotropy has been proposed, which is produced by forming a smectic liquid crystal having such properties into a thin film in a mode of coating or the like followed by solidifying it (JP-A 2000-239402 and JP-A 2003-277754). The physical properties of liquid crystals that contribute to the properties of the optical film include the birefringence, the angle between the helical axis direction of the helical structure of the liquid-crystal phase of the compound and the major axis direction of the liquid-crystal molecule, the temperature range in which the liquid crystal exhibits a smectic phase, and the easiness in having a helical structure. Heretofore, however, no one knows a smectic liquid crystal which has a large birefringence and has a large angle to be formed by the helical axis direction of the helical structure of the liquid-crystal phase of the compound and the major axis direction of the liquid-crystal molecule, and no one could attain an optical filter having satisfactory properties. Accordingly, it is earnestly desired to develop a liquid-crystal compound having such properties.

SUMMARY OF THE INVENTION

An object of the invention is to provide a liquid-crystal compound of such that its birefringence is large, the angle between the helical axis direction of the helical structure of the liquid-crystal phase of the compound and the major axis direction of the liquid-crystal molecule is large and the temperature range in which the compound exhibits a smectic phase is broad, and also to provide a liquid-crystal composition containing the compound. Another object of the invention is to provide a functional film that comprises the liquid-crystal compound or the liquid-crystal composition and has useful optical properties.

To solve the above-mentioned problems, we, the present inventors have studied various liquid-crystal compounds that exhibit a smectic phase, and, as a result, have found out a group of compounds that show a high birefringence, and have reached the present invention. Specifically, the objects of the invention are attained by the following methods.

(1) A compound represented by the following formula (1) and exhibiting a smectic liquid-crystal phase:

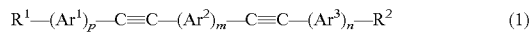

wherein $R^1$ and $R^2$ each represent an alkyl group, at least one —$CH_2$— in the alkyl group may be substituted with any of —$C\equiv C$—, —$C(R^3)=C(R^4)$—, —$CO$—, —$O$—, —$S$—, —$CO_2$—, —$OCO$—, —$CON(R^5)$—, —$N(R^6)CO$— and —$C(R^3)(-O-)C(R^4)$—; $R^3$, $R^4$, $R^5$ and $R^6$ each represent a hydrogen atom or an alkyl group; $Ar^1$, $Ar^2$ and $Ar^3$ each represent a divalent aromatic hydrocarbon group or a divalent aromatic heterocyclic group; and p, m and n each indicate 1 or 2.

(2) A liquid-crystal composition containing at least one compound of above (1).

(3) The liquid-crystal composition of above (2), wherein the smectic liquid-crystal phase is a chiral smectic liquid-crystal phase.

(4) An optical material that contains the liquid-crystal composition of above (2) or (3).

According to the invention, it is possible to obtain a liquid-crystal compound having a large birefringence and having a broad temperature range in which it shows a smectic phase, and to obtain a liquid-crystal composition containing the compound. It is also possible to make them into functional films having useful optical properties.

BEST MODE FOR CARRYING OUT THE INVENTION

The invention is described in detail herein under. In this description, the numerical range expressed by the wording "a number to another number" means the range that falls between the former number indicating the lowermost limit of the range and the latter number indicating the uppermost limit thereof.

The compound of formula (1) of the invention is described.

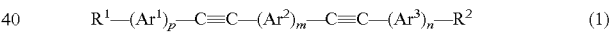

In formula (1), $R^1$ and $R^2$ each represent an alkyl group (preferably a hexyl group, a heptyl group, an octyl group, a nonyl group, a dodecyl group, a hexadecyl group, an eicosyl group), and the alkyl group preferably has from 6 to 30 carbon atoms, more preferably from 8 to 20, even more preferably from 10 to 20 carbon atoms. At least one —$CH_2$— in the alkyl group for $R^1$ and $R^2$ may be substituted with any of —$C\equiv C$—, —$C(R^3)=C(R^4)$—, —$CO$—, —$O$—, —$S$—, —$CO_2$—, —$OCO$—, —$CON(R^5)$—, —$N(R^6)CO$— and —$C(R^3)(-O-)C(R^4)$—, preferably with any of —$C\equiv C$—, —$C(R^3)=C(R^4)$—, —$CO$—, —$O$—, —$CO_2$— and —$OCO$—, more preferably with any of —$CH=CH$—, —$CO$—, —$O$— and —$CO_2$—.

—$C(R^3)(-O-)C(R^4)$— means the following:

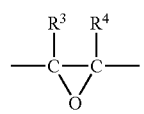

—$CH_2$— to be substituted with any of the above-mentioned groups may be in any position in the alkyl group, and two or more (—$CH_2$—)'s may be substituted. $R^3$, $R^4$, $R^5$ and $R^6$ each represent a hydrogen atom or an alkyl group. Preferably, $R^3$ and $R^4$ are a hydrogen atom, a methyl group or an ethyl group, more preferably a hydrogen atom. $R^5$ and $R^6$ are preferably a hydrogen atom or an alkyl group having from 1 to 5 carbon atoms, more preferably a methyl group or an ethyl group. $R^1$ and $R^2$ may be further substituted, and preferred examples for them are a halogen atom (e.g., fluorine, chlorine), a cyano group, and a hydroxyl group.

$Ar^1$, $Ar^2$ and $Ar^3$ each represent a divalent aromatic hydrocarbon group or aromatic heterocyclic group. Examples of the aromatic hydrocarbon group are the following:

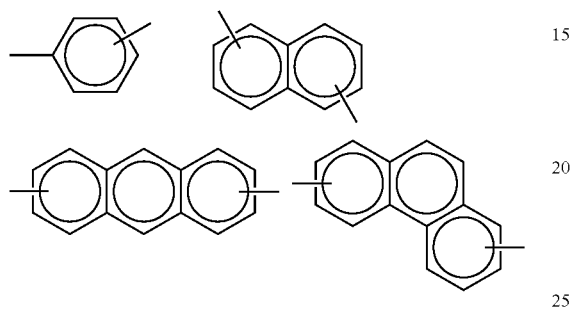

Of those, preferred are a 1,4-phenylene group, a 2,6-naphthylene group, a 2,6-anthrylene group and a 2,7-phenanthrylene group; and more preferred is a 1,4-phenylene group.

When $Ar^1$, $Ar^2$ and $Ar^3$ each represent a divalent aromatic heterocyclic group, then the aromatic heterocyclic group is preferably an aromatic 5-membered heterocyclic group or an aromatic 6-membered heterocyclic group, and its examples are the following:

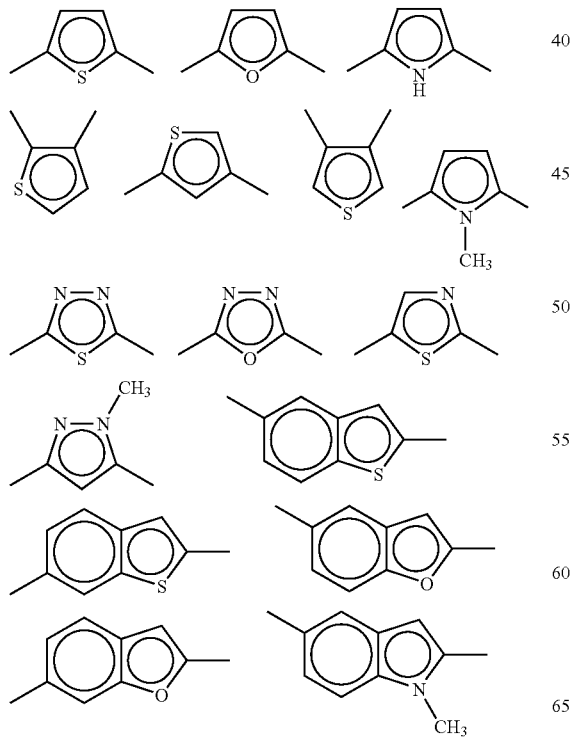

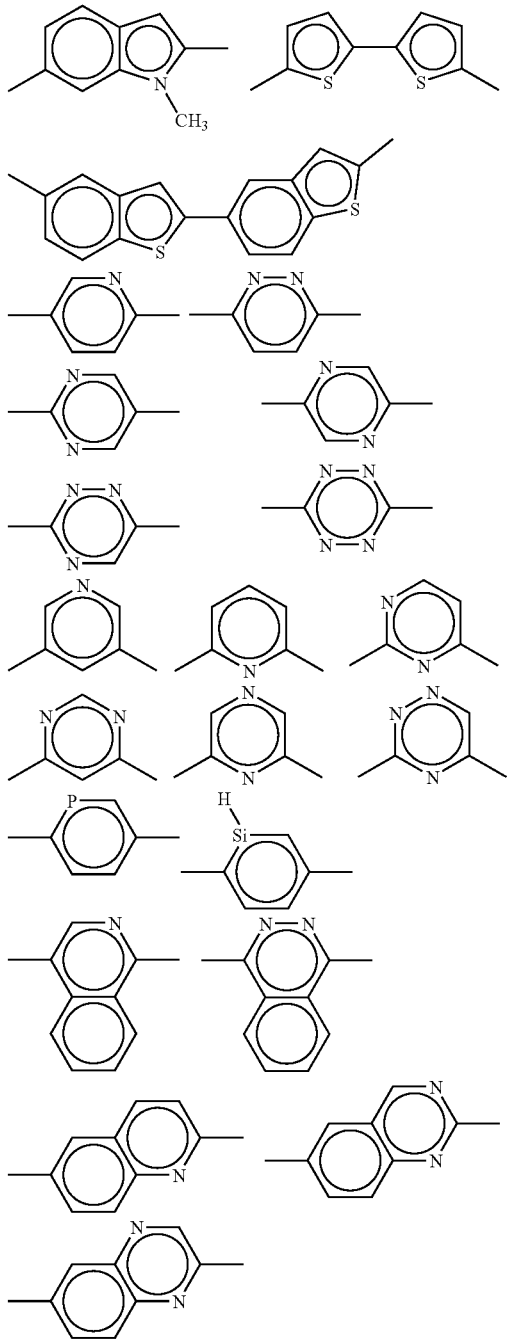

Of those, preferred is a nitrogen-containing 6-membered ring that bonds to the formula at the p-position; and more preferred is a pyridine ring that bonds to it at 2,5-position, or a 1,3-pyrimidine ring or a 1,4-pyrimidine ring that bonds to it at 2,5-position.

The group for $Ar^1$, $Ar^2$ and $Ar^3$ may be further substituted, and its substituents include a halogen atom (e.g., fluorine, chlorine), a cyano group, an alkyl group having from 1 to 3 carbon atoms (e.g., methyl, ethyl), an alkoxy group having from 1 to 3 carbon atoms (e.g., methoxy), and an alkylthio group having from 1 to 3 carbon atoms (e.g., methylthio). These substituents may have a possible number of substituents, but the number of the substituents for them is from 0 to 2, more preferably 0 or 1. One example of the substituted substituents is an alkyl group having from 1 to 3 carbon atoms and substituted with a halogen atom, preferably a perfluoroalkyl group.

Preferably, the compound of the invention has a birefringence of at least 0.20, more preferably from 0.20 to 0.40. Also preferably, the liquid-crystal compound of the invention is such that the angle between the helical axis direction of the helical structure of the liquid-crystal phase of the oriented compound and the major axis direction of the liquid-crystal molecule is from 15° to 80°.

Examples of the compound of formula (1) are mentioned below, to which, however, the invention should not be limited.

(1)
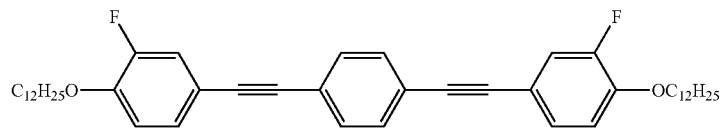

(2)
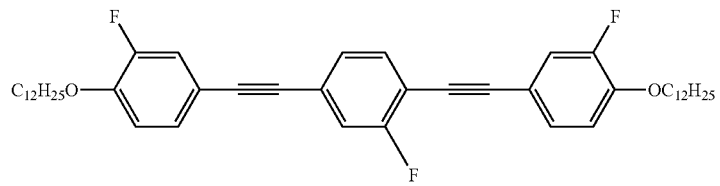

(3)
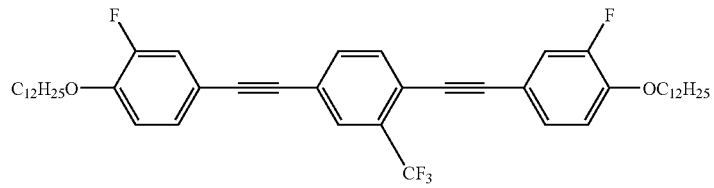

(4)
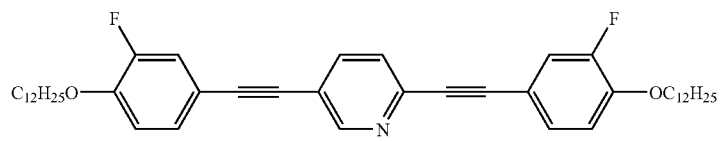

(5)
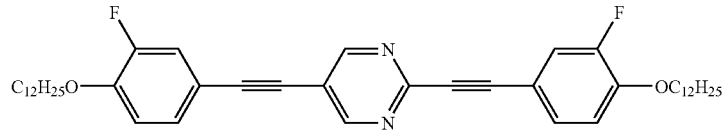

(6)
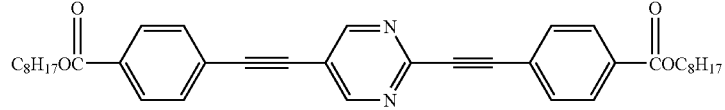

(7)
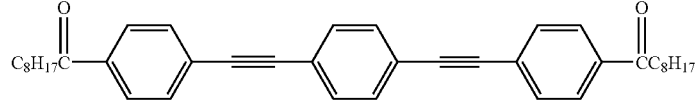

(8)
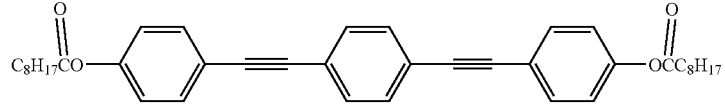

(10)
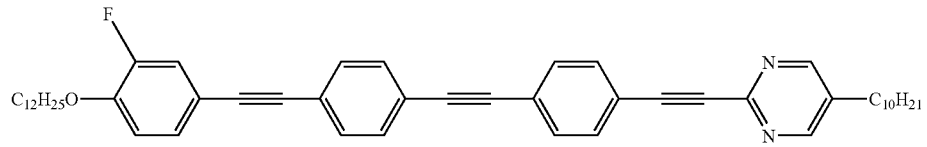

-continued

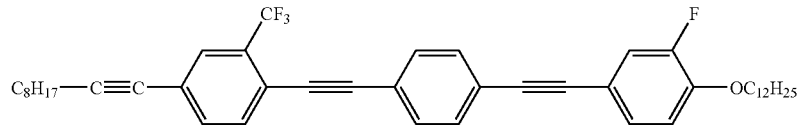
(11)

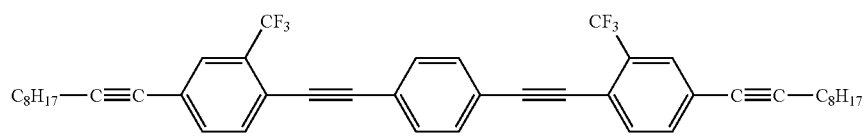
(12)

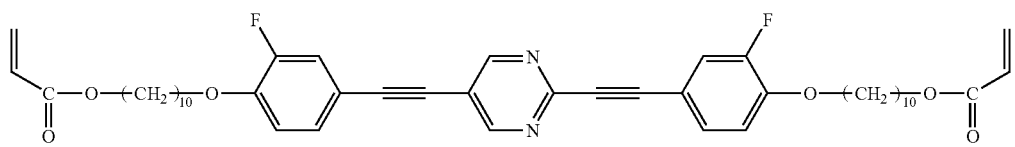
(13)

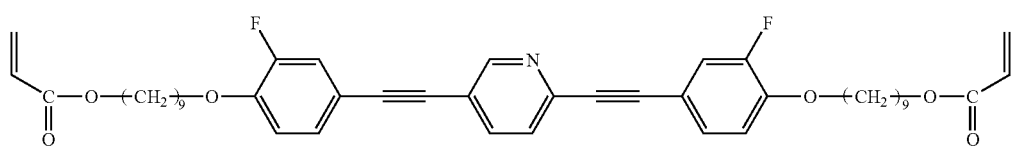
(14)

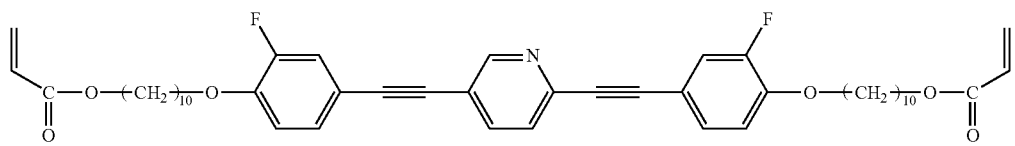
(15)

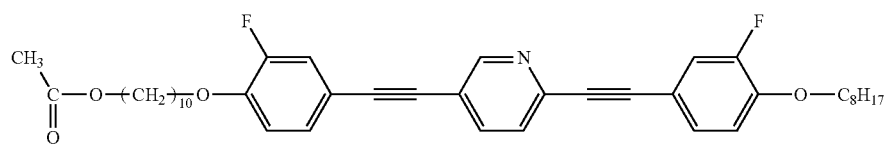
(16)

The compound of formula (1) may be produced, for example, according to the method described in *Macromolecules*, Vol. 26, p. 5840 (1993) or in JP-A 2000-198755. The production of the compound of formula (1) is concretely demonstrated in the Examples given hereinunder.

The liquid-crystal compound of the invention may be combined with any known liquid-crystal compound.

When the compound of the invention is combined with a chiral agent, then it can exhibit a chiral smectic phase. The chiral agent is described in JP-A 7-118202, 8-120271, 10-158268; JP-T 2000-515496 (the term "JP-T" as used herein means a published Japanese translation of a PCT patent application); and Japanese Patent Application No. 2003-330304. When combined, the amount of the chiral agent may be from 0.01% to 20% (by mass) of the liquid-crystal compound of formula (1) of the invention.

EXAMPLES

The invention is described more concretely with reference to the following Examples. The material, the amount, the blend ratio, the treatment and the process employed in the following Examples may be varied in any desired manner not overstepping the sprit and the scope of the invention. Accordingly, the scope of the invention should not be limited to the following Examples.

Production Example 1 Production of Compound (4)

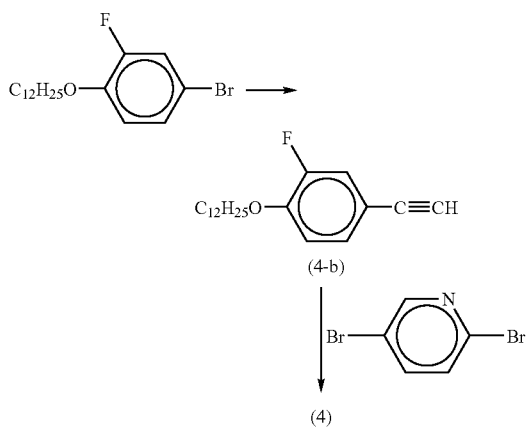

A mixture comprising compound (4-a) (83.5 mmol), acetonitrile (170 ml), trimethylsilylacetylene (92 mmol), piperidine (334 mmol), triphenylphosphine (hereinafter referred to as TPP) (1.25 mmol), CuI (0.3 mmol) and bistriphenylphosphine palladium chloride (hereinafter referred to as TPC) (0.25 mmol) was reacted in a nitrogen atmosphere at 70° C. for 2 hours. Next, TPC (0.25 mmol) and trimethylsilylacetylene (36 mmol) were added to it, and further reacted for 5 hours. This was cooled to room temperature, and ethyl acetate (300 ml) was added to it, and the organic layer was washed twice with 1 mol/L hydrochloric acid and then concentrated. The residue was purified through silica gel column chromatography (eluent: hexane). The thus-obtained substance was put into methanol (140 ml), and potassium carbonate (82.5 mmol) was added to it and then stirred at room temperature for 5 hours. Ethyl acetate (300 ml) was added to it, and washed with 1 mol/L hydrochloric acid, aqueous sodium hydrogencarbonate solution and saline solution, and then concentrated to obtain compound (4-b) (yield: 76%).

Compound (4-b) (7 mmol) and 2,5-dibromopyridine (3.5 mmol) were mixed in acetonitrile (10 ml). In a nitrogen atmosphere, piperidine (14 mmol), TPP (0.105 mmol), CuI (0.025 mmol) and TPC (0.021 mmol) were added to it and reacted at 80° C. for 2.5 hours. This was cooled to room temperature, and the resulting crystal was taken out through filtration and purified through silica gel column chromatography (eluent: methylene chloride/hexane=1/1). The resulting crystal was recrystallized from isopropyl alcohol to obtain compound (4) (yield: 70%). The phase transition temperatures of the thus-obtained compound were as follows: Cr 77.0 Sc 164.5 Iso. The birefringence of the compound was $\Delta n=0.36$. The angle between the helical axis direction of the helical structure of the liquid-crystal phase of the oriented liquid crystal of the compound and the major axis direction of the liquid-crystal molecule was 41.7°.

Production Example 2 Production of Compound (15)

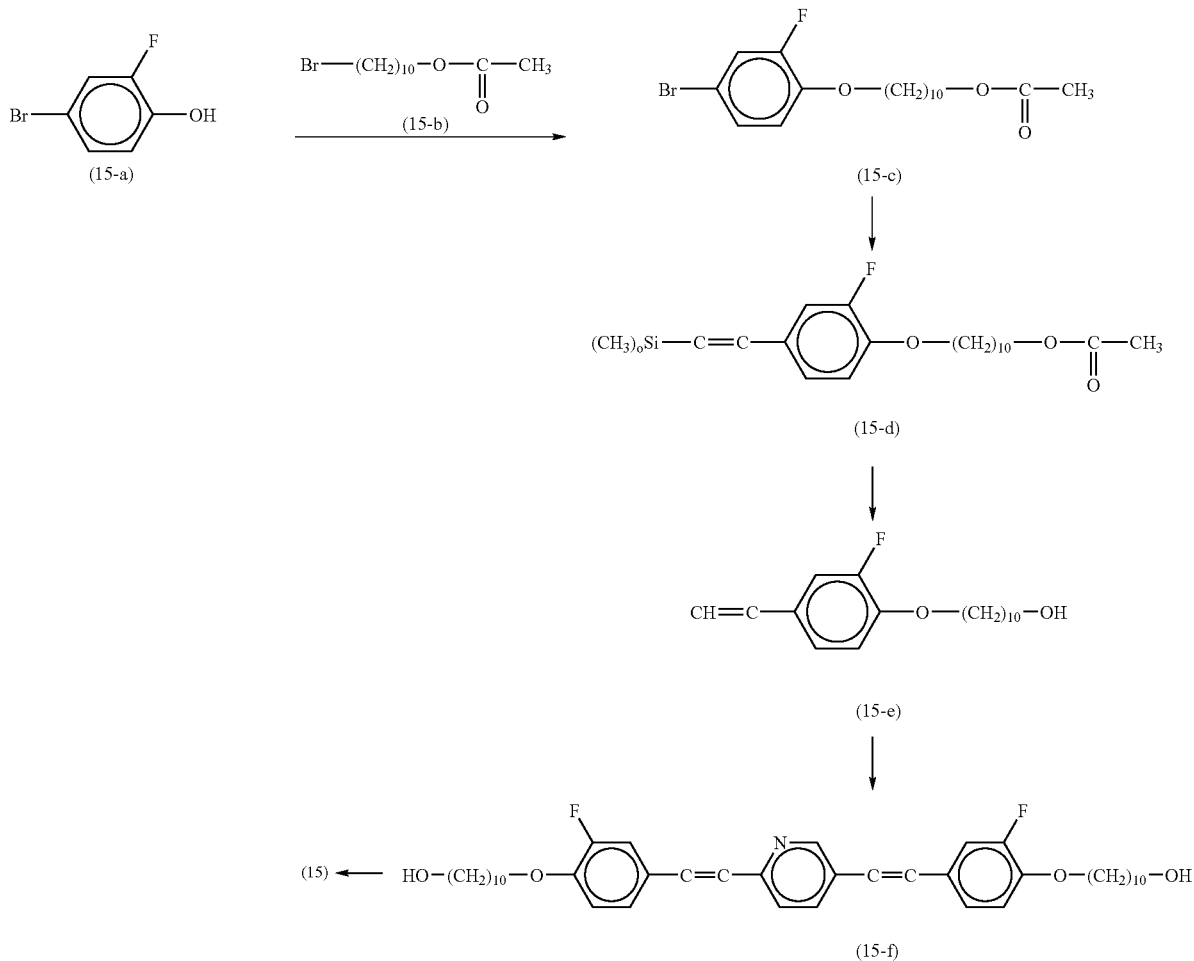

Potassium carbonate (0.196 mol) and compound (15-b) (0.137 mol) were added to N,N-dimethylacetamide (260 ml) solution of compound (15-a) (0.131 mol), and reacted at 90° C. for 6 hours. Next, ethyl acetate (300 ml) was added to it, and the insoluble was removed through filtration. The resulting filtrate was washed with 1 mol/L hydrochloric acid and concentrated, and compound (15-c) was thus quantitatively obtained.

Compound (15-c) (0.08 mol) and trimethylsilylacetylene (0.16 mol) were mixed in acetonitrile (160 ml), and piperidine (0.32 mol), TPP (4.80 mmol), CuI (1.13 mmol) and TPC (0.96 mmol) were added to it and reacted in a nitrogen atmosphere at 80° C. for 4 hours. Next, ethyl acetate (200 ml) was added to it, and the reaction solution was washed with 1 mol/L hydrochloric acid and concentrated. The resulting residue was purified through silica gel column chromatography (eluent: ethyl acetate/hexane=1/7 by volume) to obtain compound (15-d) (yield: 66.6%).

Compound (15-d) (0.04 mol) was mixed in methanol (100 ml), and potassium carbonate (0.096 mol) was added to it. This was stirred at room temperature for 1 hour, and then ethyl acetate (200 ml) was added to it, and the insoluble was removed through filtration. The resulting filtrate was concentrated, and the residue was purified through silica gel column chromatography (eluent: ethyl acetate/hexane=3/7 by volume), and compound (15-e) was thus quantitatively obtained.

Compound (15-e) (0.068 mol) and 2,5-dibromopyridine (0.034 mol) were mixed in acetonitrile (140 ml), and TPP (2.04 mmols), CuI (0.48 mmols) and TPC (0.41 mmols) were added to it and reacted in a nitrogen atmosphere at 80° C. for 2 hours. This was cooled to room temperature, and the precipitated crystal was taken out through filtration and recrystallized from acetone to obtain compound (15-f) (yield: 68.2%).

Compound (15-f) (0.8 mmol) was mixed in tetrahydrofuran (4 ml), and N,N-dimethylaniline (1.9 mmol) was added to it. This was heated at 60° C., and acrylic acid chloride (1.9 mmol) was added to it and further reacted for 1 hour. Then, this was cooled to room temperature, and water (100 ml) was added to it. The resulting crystal was taken out through filtration, and washed with acetonitrile cooled with ice. The resulting crystal was further purified through silica gel column chromatography (eluent: acetonitrile/methylene chloride=1/100 by volume) to obtain compound (15) (yield: 72%). The phase transition temperatures of the thus-obtained compound were as follows: Cr 75.5 Sc 108.8 $S_A$ 117.3 N 120.0 Iso. The birefringence of the compound was Δn=0.27. The angle between the helical axis direction of the helical structure of the liquid-crystal phase of the oriented liquid crystal of the compound and the major axis direction of the liquid-crystal molecule was 31°.

Production Example 3 Production of Compound (1)

Compound (1) was produced in the same manner as that for compound (4). The phase transition temperatures of the compound were as follows: Cr 109 SH 110.6 Sc 151.7 N 154.5 Iso. The birefringence of the compound was Δn=0.32. The angle between the helical axis direction of the helical structure of the liquid-crystal phase of the oriented liquid crystal of the compound and the major axis direction of the liquid-crystal molecule was 41°.

Production Example 4 Production of Compound (2)

Compound (2) was produced in the same manner as that for compound (4). The phase transition temperatures of the compound were as follows: Cr 97 Sc 132 N 141 Iso. The birefringence of the compound was Δn=0.31. The angle between the helical axis direction of the helical structure of the liquid-crystal phase of the oriented liquid crystal of the compound and the major axis direction of the liquid-crystal molecule was 37°.

Production Example 5 Production of Compound (5)

Compound (5) was produced in the same manner as that for compound (4). The phase transition temperatures of the compound were as follows: Cr 115.2 Sc 164.5 Iso. The birefringence of the compound was Δn=0.34. The angle between the helical axis direction of the helical structure of the liquid-crystal phase of the oriented liquid crystal of the compound and the major axis direction of the liquid-crystal molecule was 43°.

Production Example 6 Production of Compound (6)

Compound (6) was produced in the same manner as that for compound (4). The phase transition temperatures of the compound were as follows: Cr 145.7 Sc 158.3 $S_A$ 162.5 Iso. The birefringence of the compound was Δn=0.38. The angle between the helical axis direction of the helical structure of the liquid-crystal phase of the oriented liquid crystal of the compound and the major axis direction of the liquid-crystal molecule was 29.5°.

Production Example 7 Production of Compound (13)

Compound (13) was produced in the same manner as that for compound (15). The phase transition temperatures of the compound were as follows: Cr 73.8 Sc 111.3 $S_A$ 117.3 Iso. The birefringence of the compound was Δn=0.26. The angle between the helical axis direction of the helical structure of the liquid-crystal phase of the oriented liquid crystal of the compound and the major axis direction of the liquid-crystal molecule was 30.7°.

Production Example 8 Production of Compound (14)

Compound (14) was produced in the same manner as that for compound (15). The phase transition temperatures of the compound were as follows: Cr 94.4 Sc 106 $S_A$ 113.9 N 125.8 Iso. The birefringence of the compound was Δn=0.26.

The invention is described more in detail with reference to the following Application Examples, in which the properties of the smectic liquid crystal of the invention are compared with those of known smectic liquid crystals to clarify the superiority of the compound of the invention to the known compounds.

Application Example 1 Application to Selective Reflection Film 10 mas. % chloroform solution of a mixture prepared by mixing compound (15) (birefringence Δn=0.27) and 15% by mass, relative to compound (15), of the following chiral agent (A) was applied onto a polyethylene terephthalate film, and dried thereon. After thus dried, the thickness of the liquid-crystal layer was 2 μm. Next, this was heated up to 125° C., and then cooled to 70° C. at a rate of −5° C./min, and thereafter further cooled gradually at a rate of −0.5° C./min. The capability of the coated sample was evaluated in point of the temperature at which it attained selective reflection of light having a center wavelength of 550 nm.

A comparative sample was prepared, using compounds described in JP-A2003-277754 (comparative compound (101), (102), (103) mentioned below). 10 mas. % chloroform solution prepared by adding 15% by mass of the following chiral agent (B) to a liquid crystal mixture (1/1/1 by mass mixture of the following comparative compounds (101), (102) and (103)) capable of forming a smectic phase was applied onto a polyethylene terephthalate film, and dried thereon. This was cooled in the same manner as above, and its capability was evaluated in point of the temperature at which the center wavelength of the light selectively reflected by the smectic phase of the coating layer was 550 nm.

Chiral Agent A:

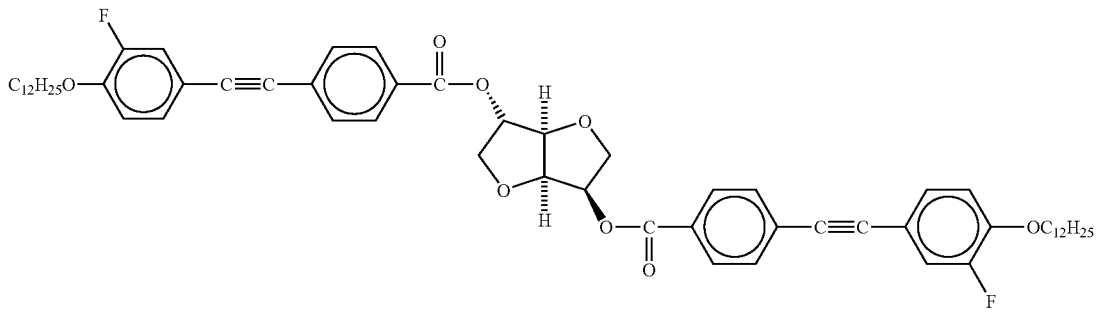

Comparative Compounds:

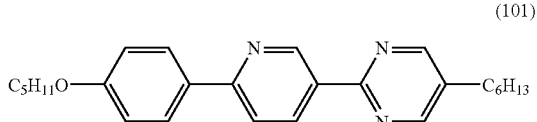
(101)

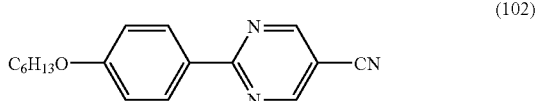
(102)

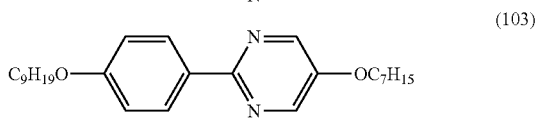
(103)

Chiral Agent B:

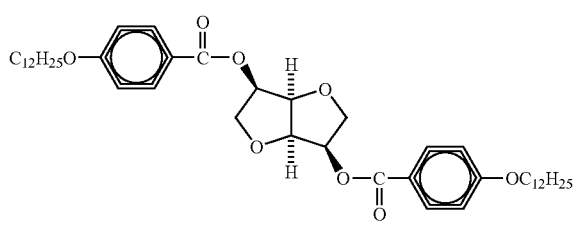

As a result, the sample prepared by the use of the compound of the invention attained selective reflection of light falling within a wavelength range of about 75 nm; but the comparative sample prepared by the use of the known liquid-crystal compounds attained selective reflection of light falling within a wavelength of about 35 nm. The result confirms the usefulness of the compound of the invention.

Application Example 2 Application to Collimator

A commercially-available coating liquid for vertical-oriented film (LQ-1800, by Hitachi Kasei DuPont) was applied onto a glass substrate having a thickness of 0.5 mm in a mode of spin coating, and then heated at 250° C. for 1 hour to form an oriented film thereon. Two substrates thus coated with the oriented film were paired in such a manner that the oriented film of the two could face inside, and these were bonded to each other with an adhesive containing a 10 μm spacer added thereto.

Compound (15) (birefringence Δn=0.27) and the chiral agent (A) (15% by mass relative to compound (15)) were injected between the two substrates, and this was cooled to 70° C. at a rate of −5° C./min, and then further cooled gradually at −0.5° C./min. The capability of the sample was evaluated in point of the product of the length of the period P of the helical structure and the mean refractive index n thereof, (p×n) of 1200 nm. A comparative sample was fabricated as follows: A mixture prepared by adding 15% by mass of the chiral agent (B) to the liquid crystal mixture used in Application Example 1 (1/1/1 by mass mixture of comparative compounds (101), (102) and (103)) was injected between the two substrates, and this was cooled in the same manner as above so as to have a product (P×n) of 1200 nm.

These samples both exhibited selective color reflection to oblique incident light. On the other hand, they transmitted vertical incident light, and they expressed the function as a collimator. The two samples were compared with each other in point of their capability. It has been found that the sample comprising the liquid crystal of the invention transmits light having a broader wavelength range, and this confirms the superiority of the liquid crystal of the invention.

The present disclosure relates to the subject matter contained in Japanese Patent Application No. 067079/2004 filed on Mar. 10, 2004, which is expressly incorporated herein by reference in its entirety.

The foregoing description of preferred embodiments of the invention has been presented for purposes of illustration and description, and is not intended to be exhaustive or to limit the invention to the precise form disclosed. The description was selected to best explain the principles of the invention and their practical application to enable others skilled in the art to best utilize the invention in various embodiments and various modifications as are suited to the particular use contemplated. It is intended that the scope of the invention not be limited by the specification, but be defined claims set forth below.

What is claimed is:

1. A compound represented by the following formula (1) and exhibiting a smectic liquid-crystal phase:

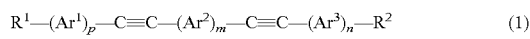

wherein $R^1$ and $R^2$ each represent an alkyl group having at least 10 carbon atoms, wherein at least one —$CH_2$— in the alkyl group may be substituted with any of —C≡C—, —C($R^3$)=C($R^4$)—, —CO—, —O—, —S—, —$CO_2$—, —OCO—, —CON($R^5$)—, —N($R^6$)CO— and —C($R^3$)(—O—)C($R^4$)—; $R^3$, $R^4$, $R^5$ and $R^6$ each represent a hydrogen atom or an alkyl group; $Ar^1$ and $Ar^3$ each represent a halogen-substituted divalent aromatic hydrocarbon group; $Ar^2$ represents a nitrogen-containing 6-membered heterocyclic group; and p, m and n each indicate 1 or 2.

2. The compound of claim 1, wherein $R^1$ and $R^2$ in the formula (1) each represent a dodecyl group, a hexadecyl group or an eicosyl group.

3. The compound of claim 1, wherein $R^1$ and $R^2$ in the formula (1) each represent an alkyl group having from 10 to 30 carbon atoms.

4. The compound of claim 1, wherein $R^1$ and $R^2$ in the formula (1) each represent an alkyl group having from 10 to 20 carbon atoms.

5. The compound of claim 1, wherein at least one —$CH_2$— in the alkyl group for $R^1$ and $R^2$ in the formula (1) is substituted with any of —C≡C—, —C($R^3$)=C($R^4$)—, —CO—, —O—, —S—, —$CO_2$—, —OCO—, —CON($R^5$)—, —N($R^6$)CO— and —C($R^3$) (—O—)C($R^4$)—.

6. The compound of claim 1, wherein at least one —$CH_2$— in the alkyl group for $R^1$ and $R^2$ in the formula (1) is substituted with any of —C≡C—, —C($R^3$)=C($R^4$)—, —CO—, —O—, —$CO_2$— and —OCO—.

7. The compound of claim 1, wherein at least one —$CH_2$— in the alkyl group for $R^1$ and $R^2$ in the formula (1) is substituted with any of —CH=CH—, —CO—, —O— and —$CO_2$—.

8. The compound of claim 1, wherein $R^3$ and $R^4$ in the formula (1) each represent a hydrogen atom, a methyl group or an ethyl group.

9. The compound of claim 1, wherein $R^3$ and $R^4$ in the formula (1) represent a hydrogen atom.

10. The compound of claim 1, wherein $R^5$ and $R^6$ in the formula (1) represent a hydrogen atom or an alkyl group having from 1 to 5 carbon atoms.

11. The compound of claim 1, wherein $R^5$ and $R^6$ in the formula (1) represent a methyl group or an ethyl group.

12. The compound of claim 1, wherein at least one of $Ar^1$, $Ar^2$ and $Ar^3$ in the formula (1) represents a 1,4-phenylene group, a 2,6-naphthylene group, a 2,6-anthrylene group or a 2,7-phenanthrylene group.

13. The compound of claim 1, wherein at least one of $Ar^1$, $Ar^2$ and $Ar^3$ in the formula (1) represents a nitrogen-containing 6-membered ring that bonds at p-position.

14. The compound of claim 1, wherein $Ar^1$, $Ar^2$ and $Ar^3$ in the formula (1) each represent a 1,4-phenylene group, a 2,6-naphthylene group, a 2,6-anthrylene group, a 2,7-phenanthrylene group or a nitrogen-containing 6-membered ring that bonds at p-position.

15. The compound of claim 1, wherein $Ar^1$, $Ar^2$ and $Ar^3$ in the formula (1) each represent a 1,4-phenylene group, a pyridine ring that bonds at 2,5-position, a 1,3-pyrimidine ring that bonds at 2,5-position or a 1,4-pyrimidine ring that bonds at 2,5-position.

16. The compound of claim 1, which is represented by any one of the following formulae:

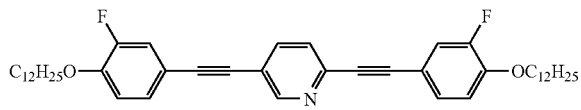

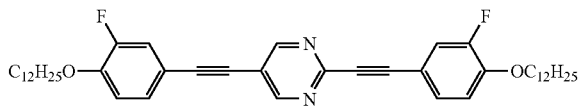

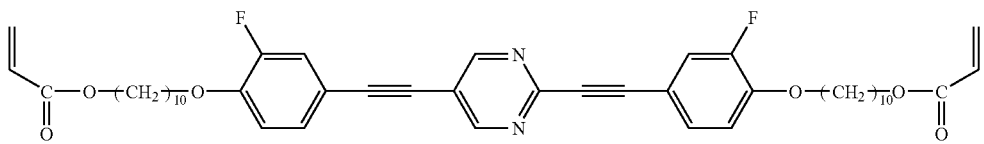

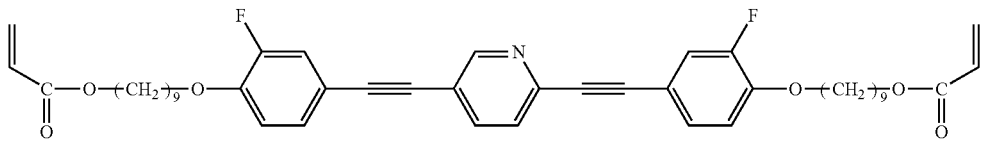

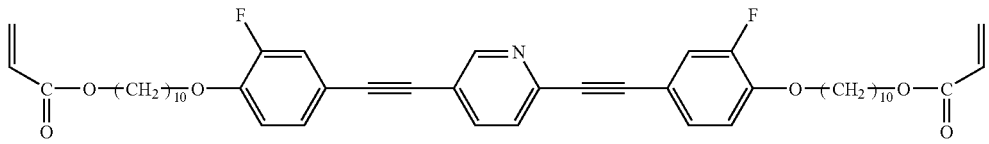

17. The compound of claim 1, which has a birefringence of from 0.20 to 0.40.

18. A liquid-crystal composition containing at least one compound of claim 1.

19. The liquid-crystal composition of claim 18, wherein a composition has a chiral smectic liquid-crystal phase.

20. An optical material that contains the liquid-crystal composition of claim 18.

* * * * *